United States Patent
Somei

(10) Patent No.: US 11,065,229 B2
(45) Date of Patent: Jul. 20, 2021

(54) METHOD FOR REDUCING ITCHING IN ATOPIC DERMATITIS

(71) Applicants: Masanori Somei, Matsudo (JP); Kazuko Somei, Matsudo (JP); Hiizu Somei, Matsudo (JP)

(72) Inventor: Masanori Somei, Chiba (JP)

(73) Assignees: Masanori Somei, Matsudo (JP); Kazuko Somei, Matsudo (JP); Hiizu Somei, Matsudo (JP)

( * ) Notice: Subject to any disclaimer, the term of this patent is extended or adjusted under 35 U.S.C. 154(b) by 0 days.

(21) Appl. No.: 16/427,266

(22) Filed: May 30, 2019

(65) Prior Publication Data
US 2020/0016122 A1 Jan. 16, 2020

(30) Foreign Application Priority Data

Jul. 11, 2018 (JP) ............. JP2018-131745

(51) Int. Cl.
| | | |
|---|---|---|
| *A01N 43/00* | (2006.01) | |
| *A01N 43/46* | (2006.01) | |
| *A61K 31/55* | (2006.01) | |
| *A61K 31/405* | (2006.01) | |
| *A61P 17/04* | (2006.01) | |
| *A61K 9/00* | (2006.01) | |

(52) U.S. Cl.
CPC ............ *A61K 31/405* (2013.01); *A61P 17/04* (2018.01); *A61K 9/0014* (2013.01)

(58) Field of Classification Search
USPC ....................................................... 546/236
See application file for complete search history.

(56) References Cited

U.S. PATENT DOCUMENTS

| 7,872,040 B2 | 1/2011 | Somei et al. |
| 9,743,647 B2 | 8/2017 | Wang et al. |

FOREIGN PATENT DOCUMENTS

| JP | 4-173777 A | 6/1992 |
| JP | 2003-137780 A | 5/2003 |
| JP | 3964417 B2 | 8/2007 |
| JP | 5380170 B2 | 1/2014 |
| JP | 5705939 B2 | 4/2015 |
| JP | 5705940 B2 | 4/2015 |

OTHER PUBLICATIONS

Chávez et al., "Tryptamine Derived Amides and Acetogenins from the Seeds of Rollinia mucosa", Journal of Natural Products, vol. 62, No. 8, pp. 1119-1122, 1999.
Hengge et al., "Adverse effects of topical glucocorticosteroids", J Am Acad Dermatol, 54, pp. 1-15, 2006.
Chavez et al., "Tryptamine Derived Amides and Acetogenins from the Seeds of Roilinia mucosa", Journal of Natural Products, vol. 62, No. 8, pp. 1119-1122, 1999.
Furue et al., "Guidelines for Management of Atopic Dermatitis", The Japanese Dermatological Association, 119 (8), pp. 1515-1534, 2009.
Hengge et al., "Adverse effects of topical glucocorticosteroids", J Am Aced Dermatol, 54, pp. 1-15, 2006.
Maeda et al., "N-Fatty acyl Tryptamines From Annona Reticulata", Phytochemistry, vol. 34, No. 6, pp. 1633-1635, 1993.

*Primary Examiner* — Layla Soroush
(74) *Attorney, Agent, or Firm* — Birch, Stewart, Kolasch & Birch, LLP

(57) ABSTRACT

This invention relates to a method for treating atopic dermatitis, comprising administering an effective amount of N-acyltryptamine represented by Formula (I):

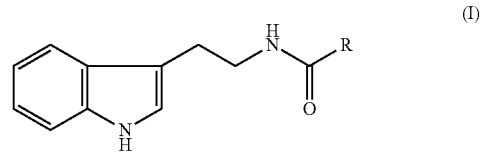

wherein R represents a saturated aliphatic hydrocarbon group having 2 to 29 carbon atoms; or a pharmaceutically acceptable salt, hydrate or solvate thereof to a subject in need thereof.

4 Claims, 2 Drawing Sheets
(2 of 2 Drawing Sheet(s) Filed in Color)

METHOD FOR REDUCING ITCHING IN ATOPIC DERMATITIS

BACKGROUND OF THE INVENTION

Field of the Invention

The present invention relates to an atopic dermatitis therapeutic agent which has a therapeutic effect equivalent to adrenocorticosteroid hormone and little side effect and exhibits an effect especially on itching.

Background Art

The number of patients with allergic diseases (allergic rhinitis, hay fever, bronchial asthma, atopic dermatitis and the like) has increased with change to the Westernized life style in recent years, and this is a great problem. Especially, atopic dermatitis is a disease frequently occurring in infants, with a prevalence of 10% or more among infants, and tends to be complicated with other atopic diseases with growth, and thus a disease about which patients and their families are very anxious.

Atopic dermatitis is characterized by being accompanied with such itching that sleep is hindered, is accompanied with scratches and wounds, and further deteriorates. Adrenocorticosteroid drugs for external application, immunosuppressive drugs for external application and oral antiallergic drugs are mainly used for the treatment thereof (Guidelines for Management of Atopic Dermatitis, The Japanese Dermatological Association, 119 (8), 1515-1534 (2009)). However, there are many cases in which the disease is poorly controlled even using these therapeutic drugs. In these cases, adrenocorticosteroid drugs for external application, which have the highest therapeutic effect, need to be used for a long period of time for the treatment. Side effects such as skin atrophy, capillary dilation, acne and hypertrichosis may appear, however (Hengge U R, Adverse effects of topical glucocorticosteroids, J Am Acad Dermatol, 54, 1-15 (2006)) when the adrenocorticosteroid drugs for external application are used continuously for a long period of time, and long-term use of the adrenocorticosteroid drugs for external application is limited. Treatment cannot therefore be performed, and many atopic dermatitis patients bear itching, pain, and lack of sleep in the present situation.

The recombinant monoclonal antibody drug, dupilumab (U.S. Pat. No. 9,743,647) was approved as an atopic dermatitis therapeutic drug for injection by FDA in 2017 and approved in Japan in January 2018. Dupilumab is expensive, however, because it is a recombinant antibody drug, and has many side effects such as serious hypersensitivity (unknown frequency), decreased blood pressure, dyspnea, atypical absence, vertigo, nausea, emesis, itching and erubescence.

The development of an atopic dermatitis therapeutic agent which stops itching, has a therapeutic effect equivalent to an adrenocorticosteroid drug for external application, little side effect and a low molecular weight, and is safe has been required due to such a situation.

Meanwhile, N-acyltryptamine is a natural product, which is isolated and structurally determined as a seed component of plants belonging to *Annona* genus (D. Chavez, L. A. Acevedo, R. Mata, J. Nat. Prod., 62, 1119-1122, (1999); U. Maeda, N. Hara, Y. Fujimoto, A. Srivastava, Y. K. Gupta, M. Sahai, Phytochemistry, 34, 1633-1635 (1993)). These plants are grown in Central America, Egypt, India, and countries in Southeast Asia, and common custard apple (*Annona reticulata*), cherimoya (*Annona cherimola*), ylang-ylang (*Cananga odorata*) and the like belong to this genus. N-Acyltryptamine derivatives are contained also in cacao (*Theobroma cacao*). These fruits are not only eaten raw but also processed into jam, marmalade, ice cream and the like, which are eaten.

For N-acyltryptamine, antidepressant and anti-stress effects (JP Patent Publication (Kokai) No. 2003-137780 A (2003)); α2 receptor blocker, a vasodilator, treatment of erectile dysfunction, and the effect of hair growth and hair increase (U.S. Pat. No. 7,872,040; JP Patent No. 3964417); melatonin antagonism (JP Patent Publication (Kokai) No. 4-173777 A (1992)); effects of preventing or improving pigmented spot and pimples (JP Patent No. 5380170); the effects of preventing or improving muscular pain, shoulder stiffness, low back pain, arthralgia and bruise pain (JP Patent No. 5705939); and the effects of preventing or improving wounds, burns, rhagades and hemorrhoids (JP Patent No. 5705940) are reported, respectively. It is not known, however, that N-acyltryptamine reduces itching and has a therapeutic effect on atopic dermatitis.

SUMMARY OF THE INVENTION

An object of the present invention is to provide an atopic dermatitis therapeutic agent which is highly safe and exhibits an effect especially on itching.

The gist of the present invention is as follows.
(1) An atopic dermatitis therapeutic agent, comprising: N-acyltryptamine represented by Formula (I):

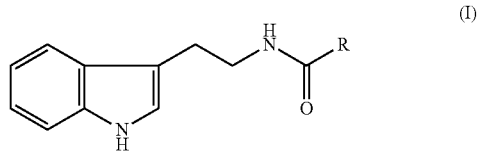

wherein R represents a saturated aliphatic hydrocarbon group having 2 to 29 carbon atoms; or a pharmaceutically acceptable salt, hydrate or solvate thereof.
(2) The atopic dermatitis therapeutic agent according to the (1), used for reducing itching in atopic dermatitis.
(3) The atopic dermatitis therapeutic agent according to the (1) or (2), wherein R is a saturated aliphatic hydrocarbon group having 6 to 17 carbon atoms in Formula (I).
(4) The atopic dermatitis therapeutic agent according to any of the (1) to (3), wherein the atopic dermatitis therapeutic agent is applied as an external preparation.
(5) A method for treating atopic dermatitis, comprising administering an effective amount of N-acyltryptamine represented by Formula (I), or a pharmaceutically acceptable salt, hydrate or solvate thereof to a subject in need thereof.

According to the present invention, an atopic dermatitis therapeutic agent which is highly safe and exhibits an effect especially on itching can be provided.

BRIEF DESCRIPTION OF THE DRAWINGS

The patent or application file contains at least one color drawing. Copies of this patent or patent application publication with color drawing will be provided by the USPTO upon request and payment of the necessary fee.

DETAILED DESCRIPTION OF THE PREFERRED EMBODIMENTS

Figure 1:
FIG. 1 is photographs showing the states of the affected part (right leg) before and after treatment of a female patient (Treatment Example 2) who used an atopic dermatitis therapeutic agent of the present invention (cream) for about 8 months.

Examples of the saturated aliphatic hydrocarbon group represented by R in Formula (I) and having 2 to 29 carbon atoms include saturated aliphatic hydrocarbon groups having 2 to 29 carbon atoms such as linear or branched C2-29-alkyl groups such as an ethyl group, a propyl group, an isopropyl group, a butyl group, an isobutyl group, a sec-butyl group, a tert-butyl group, a pentyl group, an isopentyl group, a hexyl group, a heptyl group, an octyl group, a nonyl group, a decyl group, the undecyl group, a dodecyl group, a tridecyl group, a tetradecyl group, a pentadecyl group, a hexadecyl group, a heptadecyl group, an octadecyl group, a nonadecyl group, an icosyl group, a henicosyl group and a docosyl group.

As the saturated aliphatic hydrocarbon group having 2 to 29 carbon atoms, a saturated aliphatic hydrocarbon group having 6 to 17 carbon atoms is preferable. Especially, N-nonanoyltryptamine, in which the saturated aliphatic hydrocarbon group represented by R in Formula (I) and having 2 to 29 carbon atoms is an octyl group having 8 carbon atoms, exhibits the strongest effect, and can implement suitably.

Examples of the pharmaceutically acceptable salt of the compound represented by Formula (I) include a salt with an inorganic acid such as hydrochloric acid, sulfuric acid, phosphoric acid, hydrobromic acid, hydriodic acid, nitric acid, pyrosulfuric acid or metaphosphoric acid; or an organic acid such as citric acid, benzoic acid, acetic acid, propionic acid, fumaric acid, maleic acid or sulfonic acid (for example, methanesulfonic acid, p-toluenesulfonic acid or naphthalenesulfonic acid).

The compound represented by Formula (I) is a known compound, can be prepared by synthesis or extraction from plants, and can be synthesized, for example, by reacting tryptamine and various halides of carboxylic acids or reacting tryptamine and various carboxylic acids in the coexistence of a carboxylic acid activator (K. Yamada, Y. Tanaka, M. Somei, Heterocycles, 79, 635-645 (2009)).

A mixture of N-acyltryptamine can be obtained by extracting from seeds or fruits of plants containing the compound represented by Formula (I), *Annona* plants (for example, common custard apple (*Annona reticulata*), cherimoya (*Annona cherimola*), sweetsop (*Annona squamosa*), ylang-ylang (*Cananga odorata*) or cacao (*Theobroma cacao*)) with aqueous ethanol and then purifying the extract by column chromatography, for example, according to the method described in D. Chavez, L. A. Acevedo, R. Mata, J. Nat. Prod., 62, 1119-1122 (1999). This mixture may be used as the active ingredient of the atopic dermatitis therapeutic agent of the present invention as it is.

Since fruits of the plants containing N-acyltryptamine as a natural product are eaten, the safety thereof is proved. The present inventors performed single oral dose toxicity tests (2,000 mg/kg) for N-nonanoyltryptamine over 14 days using Kwl:ICR mice. No abnormality was found in anatomical observation at all, and it was found that the lethal dose was 2,000 mg/kg or more and thus N-acyltryptamine is a safe compound (LIFE SCIENCE LABORATORIES, LTD. 5-19, 2-chome, Nishihonmachi, Nishi-ku, Osaka-shi, Osaka-fu, New Okazakibashi building, April 2011). Patch tests were performed on human skin, the skin irritation index was 0.0, and the safety was confirmed (LIFE SCIENCE LABORATORIES, LTD., June 2011). It was further found in an experiment in Nei Mongol, China that even when N-nonanoyltryptamine was administered at a dose of 1.0 mg/50 kg/day over 4 years to increase cashmere of goats, there was no abnormality at all, it had a strong breeding effect, and the amount of cashmere was increased at a weight ratio of 1.2 to 1.7 (based on the M. Somei, Heterocycles, 75, 1021-1053 (2008) and the experimental result thereafter for two years). The safety of N-acyltryptamine was confirmed from these results.

Since the atopic dermatitis therapeutic agent of the present invention is highly safe as described above, it can be administered alone or in any dosage form obtained by mixing it with other pharmaceuticals, or an optional carrier for preparations, an optional diluent, an optional coating agent or the like. Although an oral, parenteral, transrectal or percutaneous administration route or any other administration route can be used as an administration method, it is preferable to apply it as an external preparation. For oral administration, examples of the preparation include powders, tablets, granules, capsules and oral liquid preparations. For parenteral administration, examples of the preparation include injections and external preparations (liquid preparations, ointments, creams, liniments, patches, sprays and the like). For transrectal administration, examples of the preparation include suppositories and capsules. The preparation methods for these can be according to known methods.

The content of N-acyltryptamine in the atopic dermatitis therapeutic agent of the present invention is not limited, since the optimum amount differs depending on the dosage form. The content per preparation is, however, adjusted generally to 0.001% by weight to 10% by weight, preferably to 0.01 to 1% by weight.

For adults, the dose of N-acyltryptamine is 0.001 to 100 mg per 1 kg of body weight per administration per day, and preferably 0.01 to 10 mg. This amount to be used can be administered once daily, or divided into several doses and administered several times per day.

When N-acyltryptamine is applied as an external preparation such as an ointment, a cream, a liniment, a patch or a spray, the dose of N-acyltryptamine is preferably 0.001 to 100 mg per 1 kg of body weight per administration per day, and this dose can be administered once daily, or divided into several doses and administered several times per day.

The present specification encompasses the contents of the specifications of Japanese Patent Application No. 2018-131745 on which the priority of the present application is based.

EXAMPLES

Although Preparation Examples and Examples will be described to explain the present invention specifically below, the present invention is not limited to these.

(Preparation Example 1) Synthesis Method

N-Nonanoyl tryptamine was synthesized according to the method of Somei et al. (K. Yamada, Y. Tanaka, M. Somei, Heterocycles, 79, 635-645 (2009)) and used for the following Preparation Examples 3 and Examples.

(Preparation Example 2) Method for Extraction from a Plant

Fruits of sweetsop (*Annona squamosa*) produced in Indonesia were dried, and the whole was pulverized. To 50 g of this pulverized powder was added 1 L of an 80% ethanol aqueous solution. The mixture was heated to reflux for 1 hour, followed by extraction. After cooling, the extract was filtered to remove insoluble matter. The solvent was vacuum-distilled off and dried to obtain 18.4 g of a crude extract of sweetsop fruits. This crude extract was purified by column chromatography according to the method of D. Chavez et al. (D. Chavez, L. A. Acevedo, R. Mata, J. Nat. Prod., 62, 1119-1122 (1999)) to obtain a mixture of N-acyl-tryptamine.

(Preparation Example 3) Preparation of Atopic Dermatitis Therapeutic Agent

Cream: A cream was prepared by mixing N-nonanoyltryptamine with a mixture of glycerin, xanthan gum, stearic acid, squalane, pentylene glycol, hydrogenated palm oil and the like so that the concentration of N-nonanoyltryptamine was 0.1% by weight. The concentration of N-nonanoyltryptamine may also be changed in the range of 0.1 to 10% by weight. Various solvents and additives may also be mixed.

Powder: A powder was prepared by mixing N-nonanoyltryptamine with galactose so that the concentration of N-nonanoyltryptamine was 0.5% by weight. It may be mixed with various diluting materials in addition to galactose. The concentration of N-nonanoyltryptamine may also be changed in the range of 0.1 to 10% by weight.

Spray: N-nonanoyltryptamine was dissolved in ethanol and water so that the concentration of N-nonanoyltryptamine was 0.2% by weight. Various solvents and additives may be added besides ethanol and water. The concentration of N-nonanoyltryptamine may also be changed in the range of 0.1 to 10% by weight.

(Example 1) Treatment Example 1 Using Cream

Patient: 49-Year-Old Male
Course:
(1) The patient got atopic dermatitis at the age of seven. Although he had received various treatments such as steroid since then, he could not sleep due to intense irritation. He has suffered for 40 years.
(2) The cream of Preparation Example 3 was purchased, and a suitable amount thereof was applied to the affected part on Aug. 4, 2016. As soon as the cream was applied, itching stopped and he stopped scratching.
"Thanks to the cream, the scratch began to heal. I could sleep at night, and I am also in better condition," he reported on August 23.
(3) "It is applied at the time of itching, and eczema disappears soon. The skin also comes to be clear," he said thankfully on the telephone on Sep. 26, 2016.
(4) On Nov. 21, 2016, the skin is in perfect condition. Work also began to succeed. The skin has also been in perfect condition since then up to the present (2018).

(Example 2) Treatment Example 2 Using Cream

Figure 2:
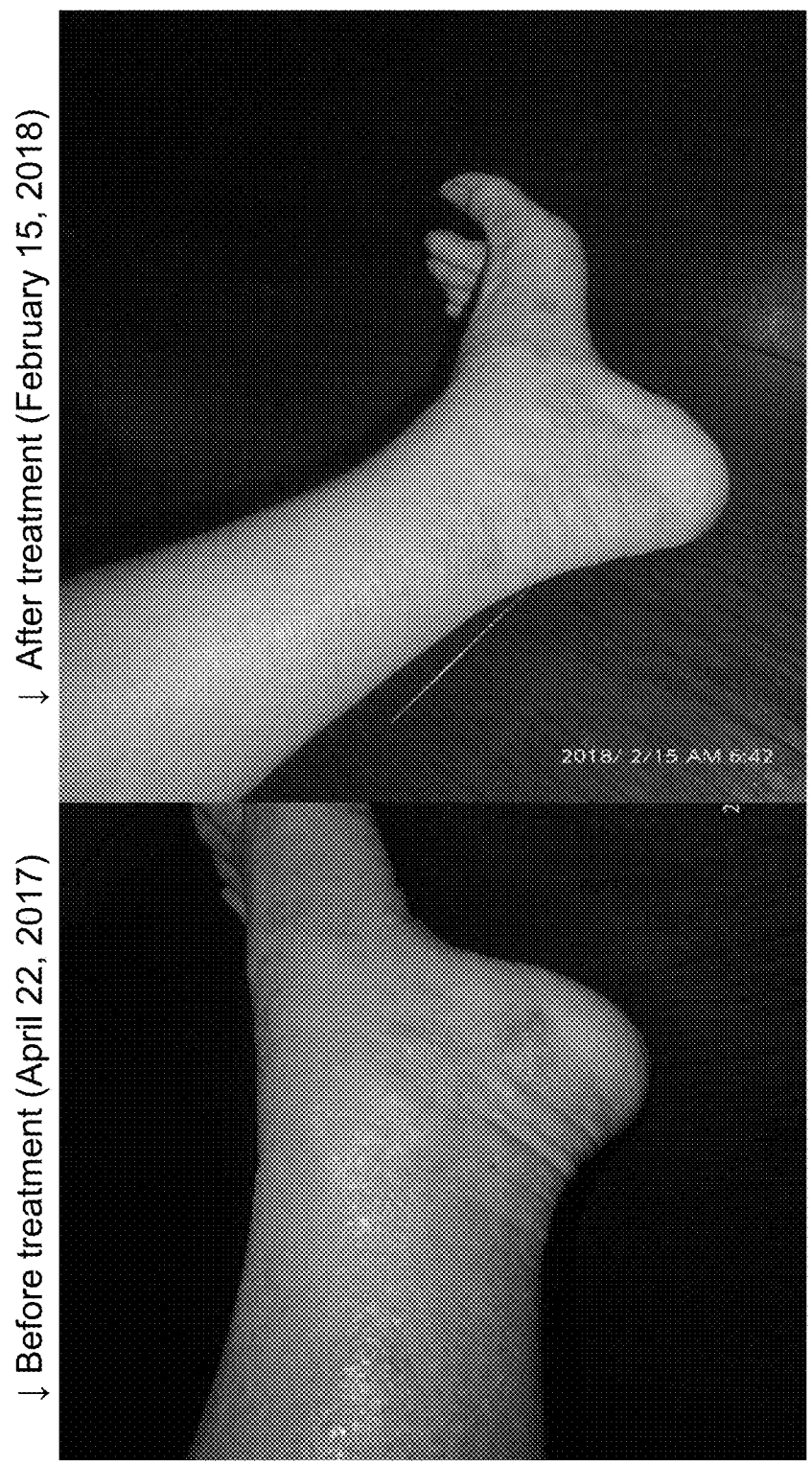
FIG. 2 is photographs showing the states of the affected part (left leg) before and after treatment of a female patient (Treatment Example 2) who used an atopic dermatitis therapeutic agent of the present invention (cream) for about 8 months.

Patient: 38-Year-Old Female
Course:
(1) Contact on Nov. 16, 2017
She got atopic dermatitis at the age of one. The whole body. Although she was hospitalized and treated by a doctor, the condition was not improved, and she has suffered since then. Many treatments such as steroid treatment, Azunol ointment, Atarax, gentamicin, and cefcapene pivoxil tablets had been performed. Since the irritation was intense and the skin was also rough, she had been continuously sleepless. Exudate leaks from bandages of the whole body, and she had had painful days.
(2) On Dec. 2, 2017, a Telephone Report was Received.
The skin condition was abated. The voice was steady and brisk differently from a timid voice in November 2017. The itching stopped by applying a suitable amount of the cream of Preparation Example 3 to the affected part, and she stopped scratching and can sleep well now.
She sends photographs every month thereafter, and the course is under observation also in 2018. The skin has improved month by month, and the skin is much better as of June 2018 than at the beginning.
FIG. 1 shows the states of the right leg before and after the treatment when the cream was used for about 8 months. FIG. 2 shows the states of the left leg.

(Example 3) Treatment Example 3 Using Cream

Report from Dermatologist:
(1) Atopic Dermatitis
The daughter of the dermatologist had atopic dermatitis. When a suitable amount of the cream of Preparation Example 3 was applied to the eczema on the face at night, the eczema improved in the morning.
(2) Other Patients
It is also used now for patients having thinned skin due to long-term external application of steroid.

(Example 4) Treatment Example 4 Using Cream and Spray

Patient: 76-Year-Old Male
Course:
(1) Especially when he lies on the left side of the body as a posture at the time of sleeping, the itching starts with a focus on the upside of the thorax of the left back. The area of itching increases with the passage of time, and he cannot bear the itching. He cannot therefore sleep due to the itching.
(2) When the cream of Preparation Example 3 was applied broadly or the spray of Preparation Example 3 was sprayed, the itching subsided in an instant, and he could sleep well.

(Example 5) Treatment Example 5 Using Cream

Patient: 44-Year-Old Female
Course:
(1) She was hospitalized due to atopic dermatitis, and the skin was thinned due to long-term steroid treatment. The treatment could not be further performed. She was obliged to leave the hospital. She could not sleep due to the itching after leaving hospital, either, and had painful days.
(2) As soon as the cream of Preparation Example 3 was applied, the itching stopped, and she could sleep. She has begun to improve since then.

(Example 6) Treatment Example 6 Using Cream

Patient: 28-Year-Old Male
Course:
(1) He had not been able to sleep well due to itching for days. Since he worked in the service industry, the influence of lack of sleep appeared, and he was embarrassed.
(2) His condition surely improved after the cream of Preparation Example 3 was used for 10 days. As soon as the cream was applied, the itching subsided. He could therefore sleep at night. The skin improved very rapidly 2 months later, and he was cured after 3 months.

(Example 7) Treatment Example 7 Using Powder

Patient: 52-Year-Old Male
Course:
(1) He had been annoyed at the itching of the whole body for dozens of years and suffered since he could not sleep enough.
(2) When he took 200 mg of the powder of Preparation Example 3 once a day, the itching stopped soon. He could sleep now well, and has been taking the same amount everyday for 1 year since then and also forgotten that he had atopic dermatitis in the past.

(Example 8) Treatment Example 8 Using Cream

Patient: 45-Year-Old Male
Course:
(1) The symptom of atopy dermatitis was seen in an area from the face to the forehead. Severe rough dry skin, scratches and a ruddy face were seen. When he began to apply the cream of Preparation Example 3, the itching stopped, and he has stopped scratching. The skin improved day by day, and has become clear skin 1 year later.

(Example 9) Treatment Example 9 Using Spray

Patient: 69-Year-Old Female
Course:
(1) A severe symptom of atopy dermatitis was seen at both ankles, and the symptom was still worse since she tore the skin.
(2) When the spray of Preparation Example 3 is sprayed, the skin is not itchy. She can also sleep well now, and is improving.

(Example 10) Treatment Example 10 Using Cream

Patient: 60-Year-Old Male
Course:
(1) The skin of the whole left leg was a little itchy, this was stressful, and the efficiency of work was falling.
(2) The symptom has been abated since he began to apply the cream of Preparation Example 3 once a day. The itching disappeared 5 months later, and he can also sleep well at night.

(Example 11) Treatment Example 11 Using Cream

Patient: 23-Year-Old Male
Progress:
(1) An area from both cheeks through the neck to the shoulders was swollen red due to atopic dermatitis.
(2) He has been applying the cream of Preparation Example 3. The itching subsided, scratches healed by degrees, and clear skin of the young man has been recovered 8 months after thereby.

(Example 12) Treatment Example 12 Using Cream

Patient: Itching Due to Insect Bite, 68-Year-Old Female
Electronic Mail from the Person Herself:
When I gardened in a break in the rain the other day, an insect bit on the ankle. Itching began from about the next day. Especially when I took a bath, sever itching appeared. It is annoying to tear the skin unconsciously while sleeping at night.
Even when MUNI alpha EX (a preparation in which prednisolone valerate acetate and diphenhydramine hydrochloride are blended) was applied, the itching subsided only temporarily. I thought what I would do if I tore the skin that night again, and thought that I had to do anything while bearing terrible itching in the bathroom on the third day. Nice idea. I will try applying the cream (the cream of Preparation Example 3).
When the cream was applied after a bath, the itching subsided promptly. I could also sleep well at night. Although Dermovate ointment 0.05% (clobetasol propionate ointment) which was given when her husband went to consult a dermatologist was also used actually, it had no effect at all.

All publications, patents, and patent applications cited in this application are intended to be incorporated herein by reference in their entirety.

What is claimed is:

1. A method for reducing itching in atopic dermatitis, comprising administering an effective amount of N-acyltryptamine represented by Formula (I):

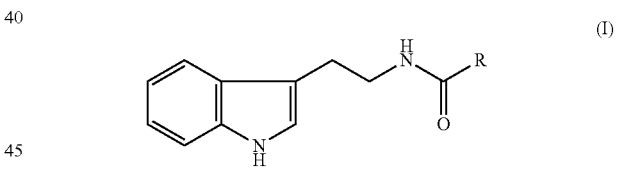

wherein R represents a saturated aliphatic hydrocarbon group having 6 to 17 carbon atoms;
or a pharmaceutically acceptable salt, hydrate or solvate thereof to a subject in need thereof.

2. The method according to claim 1, comprising administering externally the N-acyltryptamine represented by Formula (I), or a pharmaceutically acceptable salt, hydrate or solvate thereof.

3. The method according to claim 1, wherein the N-acyltryptamine represented by Formula (I) is N-nonanoyltryptamine.

4. The method according to claim 3, comprising administering externally the N-acyltryptamine represented by Formula (I), or a pharmaceutically acceptable salt, hydrate or solvate thereof.

* * * * *